United States Patent
Xu et al.

(10) Patent No.: US 12,180,476 B2
(45) Date of Patent: Dec. 31, 2024

(54) USE OF PIWI-INTERACTING RNA piR-hsa-211106

(71) Applicant: Qingdao University, Qingdao (CN)

(72) Inventors: Wenhua Xu, Qingdao (CN); Yongmei Liu, Qingdao (CN); Yanhan Dong, Qingdao (CN); Jinning Gao, Qingdao (CN); Xiaodan Hao, Qingdao (CN); Zibo Wang, Qingdao (CN); Meng Li, Qingdao (CN)

( * ) Notice: Subject to any disclaimer, the term of this patent is extended or adjusted under 35 U.S.C. 154(b) by 178 days.

(21) Appl. No.: 17/666,262

(22) Filed: Feb. 7, 2022

(65) Prior Publication Data

US 2023/0250425 A1    Aug. 10, 2023

(51) Int. Cl.
  *C12N 15/113*    (2010.01)
  *A61K 31/713*    (2006.01)
  *A61P 35/00*     (2006.01)

(52) U.S. Cl.
  CPC .......... *C12N 15/113* (2013.01); *A61K 31/713* (2013.01); *A61P 35/00* (2018.01); *C12N 2310/10* (2013.01)

(58) Field of Classification Search
  CPC .... A61P 35/00; C12N 2310/10; C12N 15/113
  See application file for complete search history.

(56) References Cited

PUBLICATIONS

Liu, Yongmei et al. "piR-hsa-211106 Inhibits the Progression of Lung Adenocarcinoma Through Pyruvate Carboxylase and Enhances Chemotherapy Sensitivity." Frontiers in oncology vol. 11 651915. Jun. 23, 2021, doi:10.3389/fonc.2021.651915 (Year: 2021).*
Liu, Y., Dou, M., Song, X. et al. The emerging role of the piRNA/piwi complex in cancer. Mol Cancer 18, 123 (2019). https://doi.org/10.1186/s12943-019-1052-9 (Year: 2019).*
Morgan, Richard "Human Tumor Xenografts: The Good, the Bad, and the Ugly." Molecular Therapy vol. 20, No. 5 (2012). https://doi.org/10.1038/mt.2012.73 (Year: 2012).*
Day, C. "Preclinical Mouse Cancer Models: A Maze of Opportunities and Challenges." Cell vol. 163, No. 1 (2015). https://doi.org/10.1016/j.cell.2015.08.068 (Year: 2015).*
Horvath, P. "Screening out irrelevant cell-based models of disease." Nature Reviews Drug Discovery vol. 15, (2016). https://doi.org/10.1038/nrd.2016.175 (Year: 2016).*
"Search Result". piRBase, 2024, http://bigdata.ibp.ac.cn/piRBase/searchResultTable.php?search_string=pir-hsa-211106&search_type=piRNA%20ID&search_result=1&class=piRNA. Accessed Mar. 25, 2024. (Year: 2024).*
"Transformant". Scitable by nature education, 2014, https://www.nature.com/scitable/definition/transformant-20/#:~:text=A%20cell%20that%20has%20received,Concept%20Links%20for%20further%20exploration. Accessed Mar. 25, 2024. (Year: 2014).*

* cited by examiner

*Primary Examiner* — Richard A Schnizer
*Assistant Examiner* — Christina Tran

(57) ABSTRACT

In the field of biomedical technology, a PIWI-interacting RNA piR-hsa-211106 is used to prepare a targeted therapeutic drug for inhibiting proliferation of lung adenocarcinoma cells. A mechanism is as follows: after the PIWI-interacting RNA piR-hsa-211106 is constructed into an agonist or a transformant, the agonist or the transformant inhibits a tricarboxylic acid cycle process by down-regulating an expression of a pyruvate carboxylase, inhibits an energy metabolism, promotes apoptosis of the lung adenocarcinoma cells, thus inhibits growth of the lung adenocarcinoma. The PIWI-interacting RNA piR-hsa-211106 directly acts on a target site and does not produce toxic and side effects and an off-target phenomenon. Large amounts of analysis and in-vivo and in-vitro experiments show that the PIWI-interacting RNA piR-hsa-211106 has high credibility and a remarkable treatment effect, and provides a new research direction for anti-tumor therapy of lung adenocarcinoma.

5 Claims, 15 Drawing Sheets

Specification includes a Sequence Listing.

USE OF PIWI-INTERACTING RNA piR-hsa-211106

SEQUENCE LISTING

The instant application contains a Sequence Listing which has been submitted electronically in ASCII format and is hereby incorporated by reference in its entirety. Said ASCII copy, created on Feb. 7, 2022, is named sequence_listing.txt and is 815 bytes in size.

TECHNICAL FIELD

The present disclosure belongs to the field of biomedical technology and specifically relates to the use of a PIWI-interacting RNA piR-hsa-211106. The PIWI-interacting RNA piR-hsa-211106 is used for inhibiting proliferation of lung adenocarcinoma cells and preparing a targeted therapeutic drug for lung adenocarcinoma.

BACKGROUND ART

Lung cancer is the most common malignant tumor. GLOBOCAN data show that there were 2.1 million new cases of lung cancers worldwide in 2018, accounting for 11.6% of all new tumor cases (ranked first); and 1.8 million deaths, accounting for 18.4% of all tumor deaths (ranked first). The lung cancer includes small cell lung cancer and non-small cell lung cancer, where the non-small cell lung cancer accounts for about 85% of all lung cancers. Besides, lung adenocarcinoma is the most common histological type of the non-small cell lung cancer, accounting for about 40-50% of pulmonary primary tumor, mostly originates from bronchial mucosa epithelium, and is mainly peripheral lung cancer. In recent years, the lung adenocarcinoma has a rising incidence. Patients may show various symptoms such as cough, blood sputum, chest pain, local wheezing, fever, and shortness of breath, depending on location and size of the tumor, degree of infiltration and compression of adjacent organs, and whether it has metastacized, and the like. The patients with lung adenocarcinoma are mostly asymptomatic in an early stage and symptoms such as emaciation, fatigue, anorexia, hoarseness, esophageal compression can be seen in a late stage. The lung adenocarcinoma which causes great burden to patients' bodies, families and society, has become a serious disease endangering human health, which is urgently need to be solved.

The pathogenesis of the lung adenocarcinoma is not clear and research shows that the occurrence of the lung adenocarcinoma is mostly related to benzopyrene. Clinically, the lung adenocarcinoma is commonly treated by excision of focus, radiotherapy and chemotherapy, molecular targeted therapy and traditional Chinese medicine. Surgery is the first choice for treating the lung adenocarcinoma, but once diagnosed, about 75% of patients with the lung adenocarcinoma are found to be in a late stage, clinically. At that time, the surgical treatment cannot be implemented, radiotherapy and chemotherapy are mainly used for delaying spread of focus, an overall curative effect and prognosis are poor, and a 5-year survival rate is lower than 20%. The drug for treating the lung adenocarcinoma in the molecular targeted therapy comprises drugs targeting angiogenesis such as bevacizumab, a COX2 suppressant, and also comprises drugs targeting epidermal growth factors, such as gefitinib, erlotinib and a HER2 suppressant. But the molecular targeted therapy is only effective against primary tumors and ineffective on metastatic tumors, which is expensive and has a low popularization rate.

About 98% RNA molecules belong to non-coding RNAs, which do not encode proteins but act directly at a RNA level. The RNAs include microRNAs (miRNAs), long non-coding RNAs (lncRNAs), PIWI-interacting RNAs (piRNAs), and the like. The piRNAs are a small non-coding RNA class first found in 2006 on male germ cells, consist of 26 to 31 nucleotides, have a 5' terminal uridine modification or a tenth adenosine bias, and do not have a distinct secondary structural region. The sequences of the piRNAs are not conserved, but a gene cluster encoding the piRNAs is extremely conserved across species. The piRNAs often form a complex with a PIWI protein and plays an important role in occurrence and development processes of diseases, such as causing methylation of specific gene loci, regulation of protein phosphorylation, silencing of a transcription product and the like. Since many piRNAs are expressed in a tissue- and stage-specific manner, maladjustment of the piRNAs can dynamically reflect a disease state. Recent research shows that a part of piRNAs in tumor cells can enter circulation through cell membranes, become new tumor markers in a body fluid and are used for early diagnosis and prognosis monitoring of the lung adenocarcinoma. Currently, there is no literature or report about regulation of a growth process of the lung adenocarcinoma in vivo by the piRNAs or using piRNAs to regulate the growth of the lung adenocarcinoma in treating the lung adenocarcinoma. Based on the fact that the piRNAs have a short molecular sequence, a full-length nucleic acid sequence is their functional motifs. The piRNAs have high specificity and a high targeting rate, and are different from other non-coding RNAs with a long sequence. Thus, the piRNAs can reduce an unforeseen off-target effect and toxic and side effects when used in treating diseases, and can promote the clinical transformation of piRNAs drugs.

SUMMARY

The present disclosure aims to design a PIWI-interacting RNA piR-hsa-211106 and the PIWI-interacting RNA piR-hsa-211106 is used to prepare a targeted therapeutic drug for inhibiting proliferation of lung adenocarcinoma cells to inhibit growth of the lung adenocarcinoma.

In order to realize the above purpose, the present disclosure relates to use of the PIWI-interacting RNA piR-hsa-211106 in preparing a targeted therapeutic drug for inhibiting proliferation of lung adenocarcinoma cells.

The PIWI-interacting RNA piR-hsa-211106 of the present disclosure is an agonist or a transformant of one selected from the group consisting of an adenovirus, a lentivirus and an adeno-associated virus, and contains a nucleotide sequence fragment shown in SEQ ID NO:1 or a nucleotide sequence fragment having a sequence similarity of greater than 80% with SEQ ID NO:1.

A mechanism of the PIWI-interacting RNA piR-hsa-211106 of the present disclosure in inhibiting proliferation of lung adenocarcinoma cells is as follows: after the PIWI-interacting RNA piR-hsa-211106 is constructed into an agonist or a transformant, the agonist or the transformant inhibits a tricarboxylic acid cycle process by down-regulating an expression of a pyruvate carboxylase, inhibits an energy metabolism, promotes apoptosis of the lung adenocarcinoma cells and realizes a targeted therapy of the lung adenocarcinoma.

The PIWI-interacting RNA piR-hsa-211106 (SEQ ID NO:1) of the present disclosure has a nucleotide sequence fragment of

TCCGGCTCGAAGGACTTCGTCTGTAATTTT;

and a primer pair is piR-hsa-211106, an upstream primer sequence piR-hsa-211106-F is

GGCTCGAAGGACTTCGTCTGT (SEQ ID NO: 2)

and a downstream primer sequence piR-hsa-211106-R is

AGTGCAGGGTCCGAGGTATT. (SEQ ID NO: 3)

A targeting effect of the PIWI-interacting RNA piR-hsa-211106 of the present disclosure is detected as follows: the PIWI-interacting RNA piR-hsa-211106 is transfected into lung adenocarcinoma cells A549 and HCC2279 and an effect of the PIWI-interacting RNA piR-hsa-211106 on a cell proliferation activity is determined by detecting proliferation indicators of lung adenocarcinoma cells by a CCK8 kit and Edu staining; an effect of the PIWI-interacting RNA piR-hsa-211106 on a cell migration capacity is determined by detecting migration indicators of the lung adenocarcinoma cells by a Transwell chamber and scratch test; and an effect of the PIWI-interacting RNA piR-hsa-211106 on apoptosis is determined by detecting apoptosis indicators by a flow cytometry.

A molecular mechanism of the PIWI-interacting RNA piR-hsa-211106 of the present disclosure in inhibiting proliferation and migration of lung adenocarcinoma cells and promoting apoptosis of the lung adenocarcinoma cells is verified through an RNA pull-down assay and a mass spectrometry technology. A result shows that the PIWI-interacting RNA piR-hsa-211106 inhibits an expression of a pyruvate carboxylase (PC), also binds to the PC and inhibits regulation of the PC on cells, and the PC is one of the most important molecules known to regulate a cell energy metabolic pathway.

When the PIWI-interacting RNA piR-hsa-211106 of the present disclosure is used to evaluate an inhibitory effect on growth of lung adenocarcinoma and a targeted therapeutic effect of the lung adenocarcinoma, an armpit percutaneous tumor-bearing model of a nude mouse is constructed. The PIWI-interacting RNA piR-hsa-211106 is injected into tumors in nude mice, negative and positive control groups are arranged at the same time and the tumor volume of the nude mice is measured regularly. A result shows that the tumor volume and weight of an experimental group are smaller than those of the control groups; and a therapeutic effect is comparable to that of the positive control group treated with cisplatin, indicating that the PIWI-interacting RNA piR-hsa-211106 has a targeted inhibitory effect on the tumor model of a nude mouse.

Compared with the prior art, the PIWI-interacting RNA piR-hsa-211106 is used to prepare a targeted therapeutic drug for inhibiting proliferation of lung adenocarcinoma cells, which provides a new research direction for preventing and treating abnormal activation of a cell energy metabolic pathway of the lung adenocarcinoma. The PIWI-interacting RNA piR-hsa-211106 inhibits tricarboxylic acid cycle by inhibiting the content of a pyruvate carboxylase, remarkably inhibits an energy metabolism and a proliferation activity and a migration capacity of the lung adenocarcinoma cells, and thus promotes apoptosis of the lung adenocarcinoma cells. The PIWI-interacting RNA piR-hsa-211106 directly acts on a target site and does not produce toxic and side effects and an off-target phenomenon. A high-throughput sequencing analysis, a mass spectrometry technology, and in-vivo and in-vitro experiments show that the PIWI-interacting RNA piR-hsa-211106 has high specificity and a high targeting rate and a less off-target effect and toxic and side effects. The PIWI-interacting RNA piR-hsa-211106 has a scientific mechanism, high credibility and a remarkable treatment effect.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

The present disclosure will be further described below with reference to the examples and accompanying drawings.

Example 1

This example related to a process of constructing an agonist with a PIWI-interacting RNA piR-hsa-211106: a PIWI-interacting RNA piR-hsa-211106 gene was used as a template, the piR-hsa-211106 was subjected to PCR amplification with primers, a double-strand PIWI protein-interacting RNA piR-hsa-211106 was produced, an antisense strand of the PIWI-interacting RNA piR-hsa-211106 was subjected to a cholesterol modification of a 3' end, four thio skeleton modification of the 3' end, two thiol skeleton modification of a 5' end and full-chain methoxy modification (Shanghai GenePharma Co., Ltd.), then an agonist was constructed.

Example 2

This example related to a process of transfecting an agonist to lung adenocarcinoma cells: after the lung adenocarcinoma cells were passaged to a cell density of about 30-50%, the agonist was transfected to the lung adenocarcinoma cells by lipo3000. 5 µl (100 pmol) of the agonist was added to an EP tube containing 95 µl of a DMEM medium by pipetting and mixing, 5 µl of lipo3000 was added to the EP tube containing 95 µl of the DMEM medium by pipetting and mixing, the two materials were mixed at a volume ratio of 1:1 to form a transfection mixture, the mixture was allowed to stand at a room temperature for 20 min and added into a culture plate, and an analysis at gene and protein levels was conducted after 48 h.

Example 3

Figure 1:
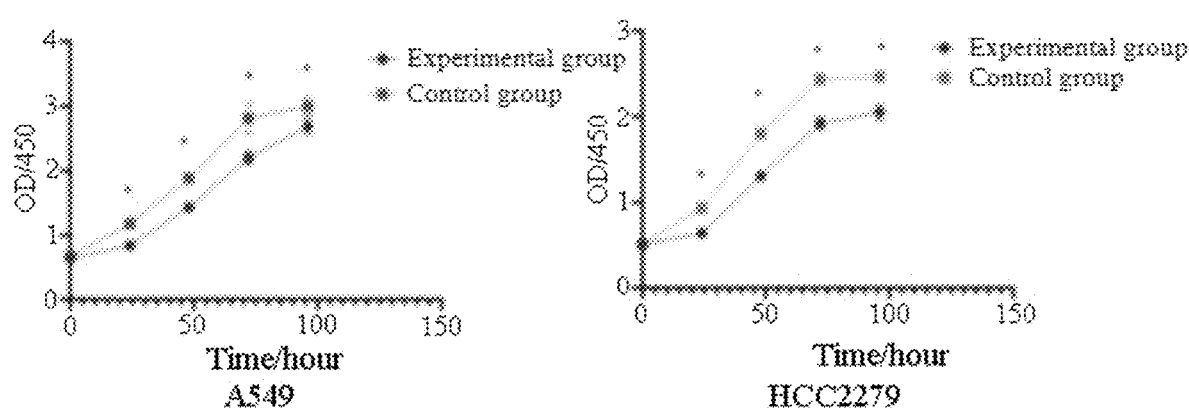
FIG. 1 is a schematic diagram of an effect of an agonist on a proliferation activity of lung adenocarcinoma cells A549 and HCC2279 detected by a CCK8 kit related in example 3 of the present disclosure.

This example related to an analysis process of a proliferation activity of lung adenocarcinoma cells A549 and HCC2279: the lung adenocarcinoma cells were cultured, the cells in an experimental group were transfected with a PIWI-interacting RNA piR-hsa-211106, 0, 1, 2, 3, and 4 days after the transfection, an original medium of the lung adenocarcinoma cells of the experimental group and a control group was respectively pipetted and discarded, the lung adenocarcinoma cells were washed with phosphate buffered saline (PBS) twice, 90 µl of a fresh medium and 10 µl of a CCK8 reagent (Vazyme Biotech Co., Ltd) were added for treatment for 1 h, an absorbance reflected by OD value was measured at 450 nm, the OD value represented cell density and reflected the cell proliferation activity, and as shown in FIG. 1, an agonist constructed by the PIWI-interacting RNA piR-hsa-211106 can significantly inhibit the proliferation of the lung adenocarcinoma cells A549 and HCC2279.

Example 4

This example related to an analysis process of a proliferation activity of lung adenocarcinoma cells A549 and HCC2279 by Edu staining: the lung adenocarcinoma cells were cultured, the cells in the experimental group were transfected with a PIWI-interacting RNA piR-hsa-211106, after transfection for two days, Edu staining was conducted (Shanghai YEASEN Biotechnology Co., Ltd) to analyze the cell proliferation:

(1) Edu labeled cells: the cells were incubated with 10 µM of an Edu working solution for 2 h at 37° C. in dark;
(2) cell fixation and permeation promotion: after the incubation was completed, a medium was removed, neutral paraformaldehyde with a mass percentage concentration of 4% was added for fixing for 15-30 min at room temperature, a fixative was removed, Triton X-100 in PBS with a mass percentage concentration of 0.5% was added, and an incubation at room temperature for 20 min was conducted to promote penetration;
(3) Edu detection: a Click-iT reaction mixture was added, a culture plate was briefly shaken to ensure that the reaction mixture covered the cells evenly, and the cells were incubated at room temperature for 30 min in dark;
(4) DNA counterstaining: 5 µg/ml of a Hoechst 33342 solution was added and an incubation was conducted in dark at room temperature for 15-30 min to stain the nucleus; and
(5) the cells were washed twice with PBS, pictures were taken with a fluorescence microscope, and a proportion of the proliferating lung adenocarcinoma cells was analyzed.

Figure 2:
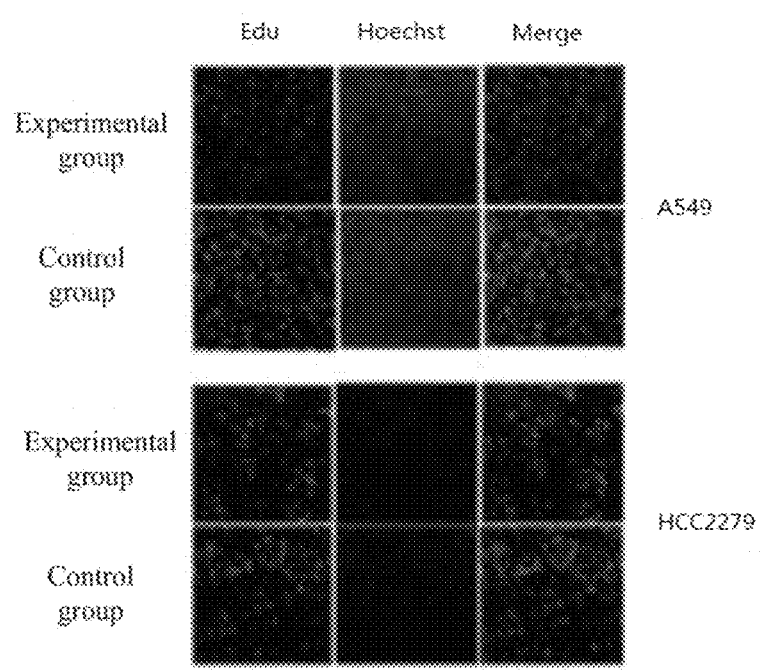
FIG. 2 is a schematic diagram of an effect of an agonist on a proliferation activity of lung adenocarcinoma cells A549 and HCC2279 detected by Edu related in example 4 of the present disclosure.
Figure 3:
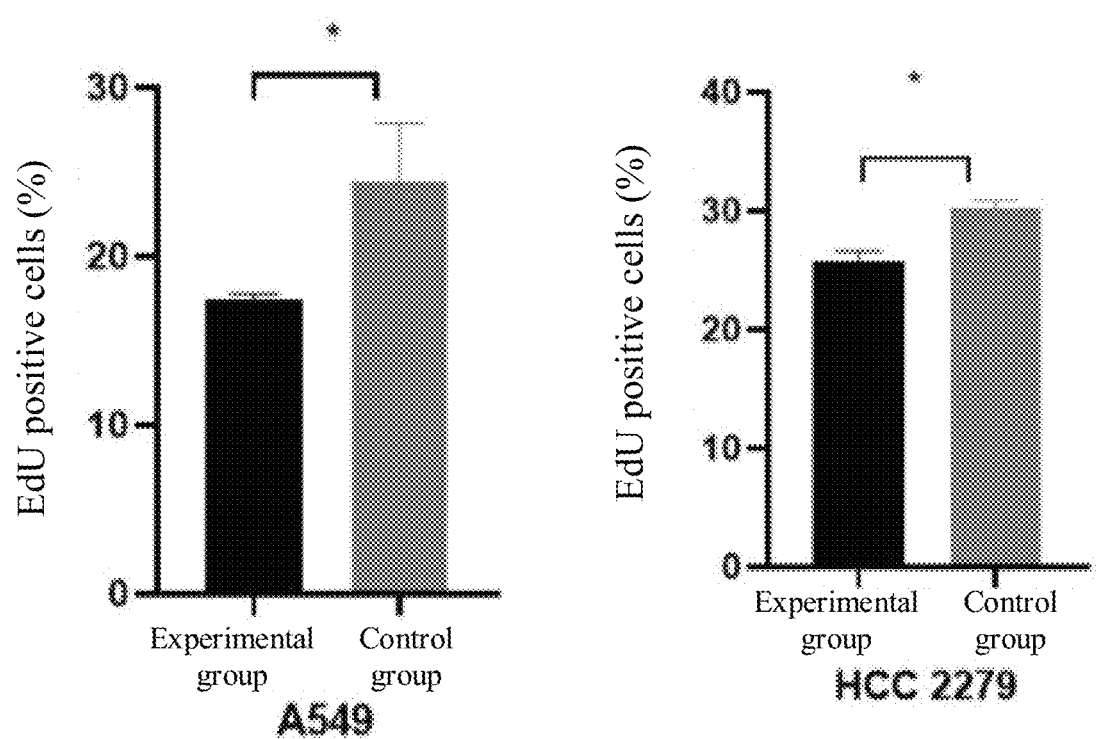
FIG. 3 is a schematic diagram of a statistical quantitative analysis results of an agonist on a proliferation activity of lung adenocarcinoma cells A549 and HCC2279 detected by Edu related in example 4 of the present disclosure.

As shown in FIGS. 2 and 3, the agonist constructed by the PIWI-interacting RNA piR-hsa-211106 can significantly inhibit the growth of the lung adenocarcinoma cells.

Example 5

Figure 4:
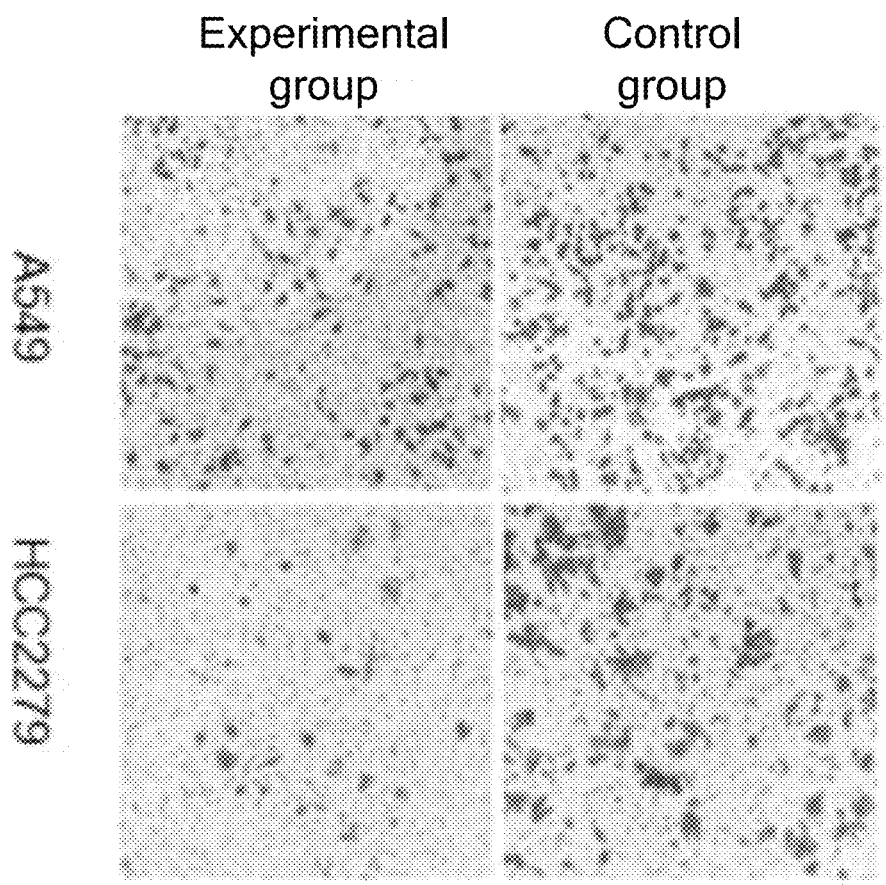
FIG. 4 is a schematic diagram of an effect of an agonist on a migration capacity of lung adenocarcinoma cells A549 and HCC2279 detected by a Transwell chamber related in example 5 of the present disclosure.
Figure 5:
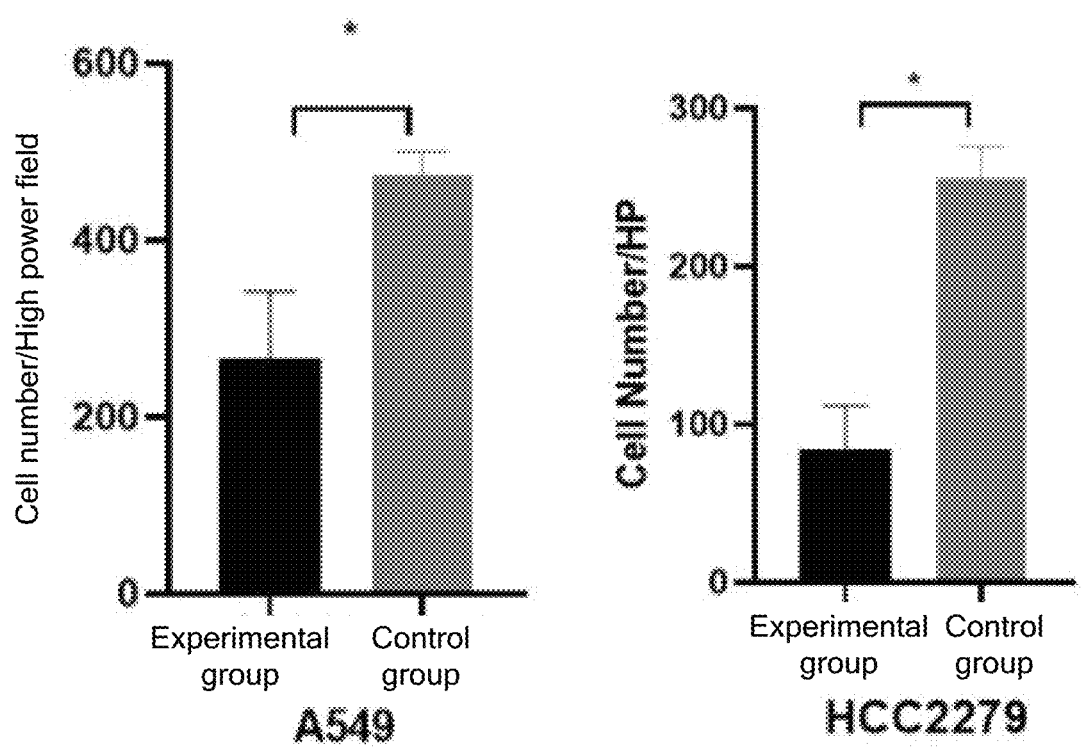
FIG. 5 is a schematic diagram of a statistical quantitative analysis results of an agonist on a migration capacity of lung adenocarcinoma cells A549 and HCC2279 detected by a Transwell chamber related in example 5 of the present disclosure.

This example related to an analysis process of a migration ability of lung adenocarcinoma cells A549 and HCC2279 by a Transwell chamber: the lung adenocarcinoma cells were cultured, the cells in the experimental group were transfected with a PIWI-interacting RNA piR-hsa-211106, after transfection for two days, the migration was measured in a 24-well Millicell chamber: 200 µl of the cells in a serum-free medium ($2 \times 10^4$) were added to a coated filter membrane, 500 µl of a medium containing 20% fetal bovine serum was added to a lower chamber as a chemoattractant, after placed in a 37° C. incubator for 24 h, the cells migrated through the filter membrane were fixed with methanol and stained with 0.5% of crystal violet, the cells were photographed and counted under a microscope, and as shown in FIGS. 4 and 5, an agonist constructed by the PIWI-interacting RNA piR-hsa-211106 can significantly inhibit the migration ability of the lung adenocarcinoma cells.

Example 6

Figure 6:
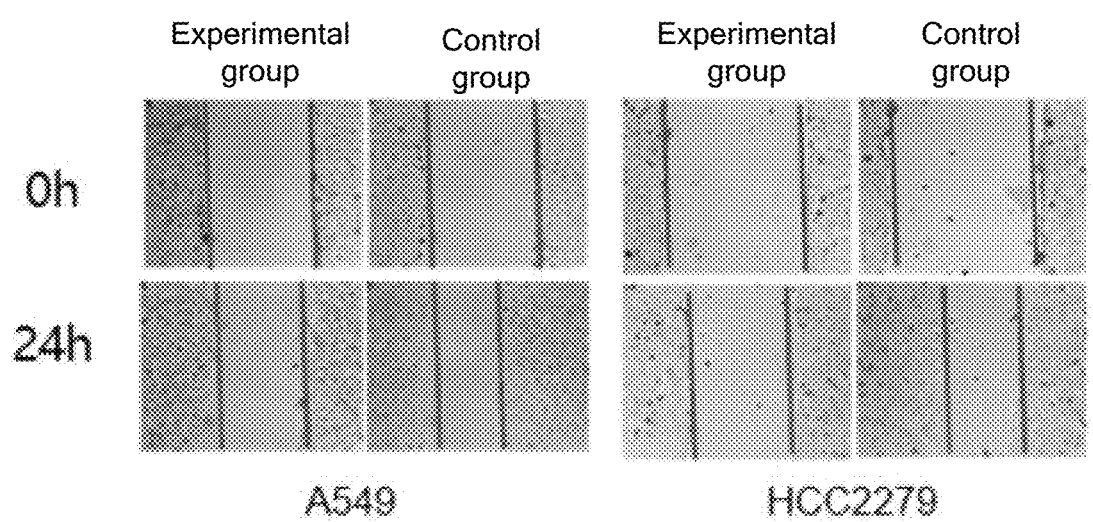
FIG. 6 is a schematic diagram of an effect of an agonist on a migration capacity of lung adenocarcinoma cells A549 and HCC2279 detected by a scratch test related in example 6 of the present disclosure.
Figure 7:
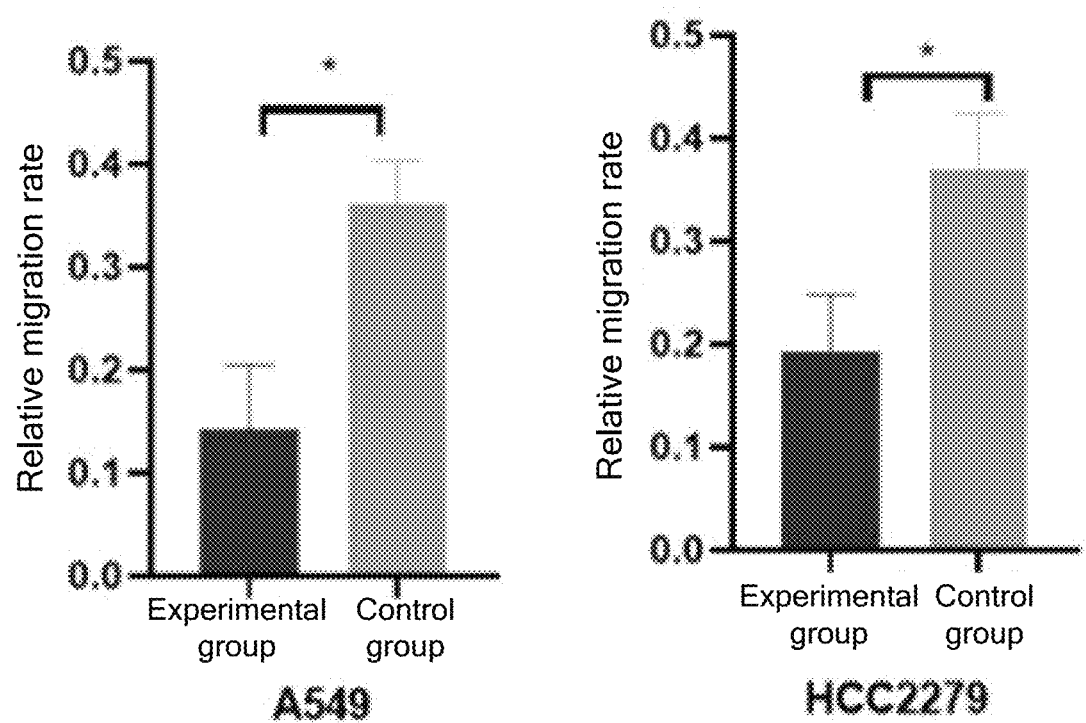
FIG. 7 is a schematic diagram of a statistical quantitative analysis results of an agonist on a migration capacity of lung adenocarcinoma cells A549 and HCC2279 detected by a scratch test related in example 6 of the present disclosure.

This example related to an analysis process of a migration ability of lung adenocarcinoma cells A549 and HCC2279 in a scratch experiment: the lung adenocarcinoma cells were cultured in a six-well plate, the cells in the experimental group were transfected with a PIWI-interacting RNA piR-hsa-211106, after transfection for two days, a cell monolayer was scratched with a 200-μl pipette tip, representative images of cell migration were captured by taking a 10× high-power field at 0 h and 24 h after scratching, a reduced distance across an induced damage area was measured and normalized to 0 h as a control to be expressed as a relative migration rate, and as shown in FIGS. 6 and 7, an agonist constructed by the PIWI-interacting RNA piR-hsa-211106 can significantly inhibit the migration ability of the lung adenocarcinoma cells.

Example 7

This example related to a detection process of apoptosis of lung adenocarcinoma cells A549 and HCC2279 by a flow cytometry: the lung adenocarcinoma cells were cultured, the cells in the experimental group were transfected with a PIWI-interacting RNA piR-hsa-211106, after transfection for two days, apoptosis was detected by Annexin V-FITC/PI (Shanghai YEASEN Biotechnology Co., Ltd):
  (1) after the lung adenocarcinoma cells were digested with a trypsin without EDTA, centrifugation was conducted at 300 g and 4° C. for 5 min and the cells were collected;
  (2) the cells were washed twice with a pre-cooled PBS, centrifugation was conducted at 300 g and 4° C. for 5 min each time and $1$-$5 \times 10^5$ cells were collected;
  (3) the PBS was pipetted and discarded, and 1× binding buffer was added to resuspend the cells;
  (4) annexin V-FITC and a PI staining solution were added, gentle mixing was conducted, and reaction was conducted in dark at room temperature for 10-15 min; and
  (5) 1× binding buffer was added, even mixing was conducted, an obtained mixture was placed on ice, and detection was conducted with the flow cytometry within 1 h.

Figure 8:
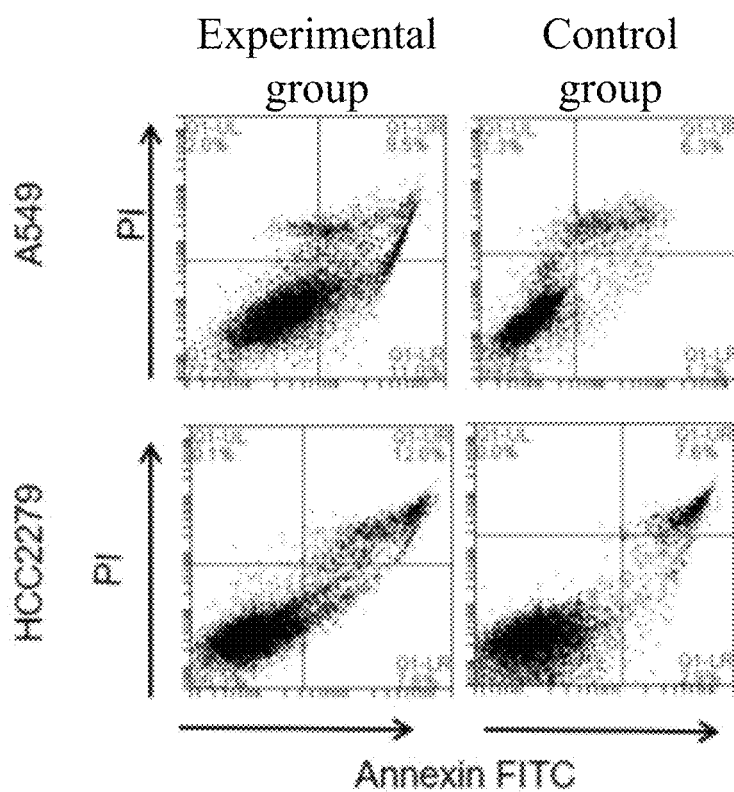
FIG. 8 is a schematic diagram of an effect of an agonist on apoptosis of lung adenocarcinoma cells A549 and HCC2279 detected by a flow cytometry related in example 7 of the present disclosure.
Figure 9:
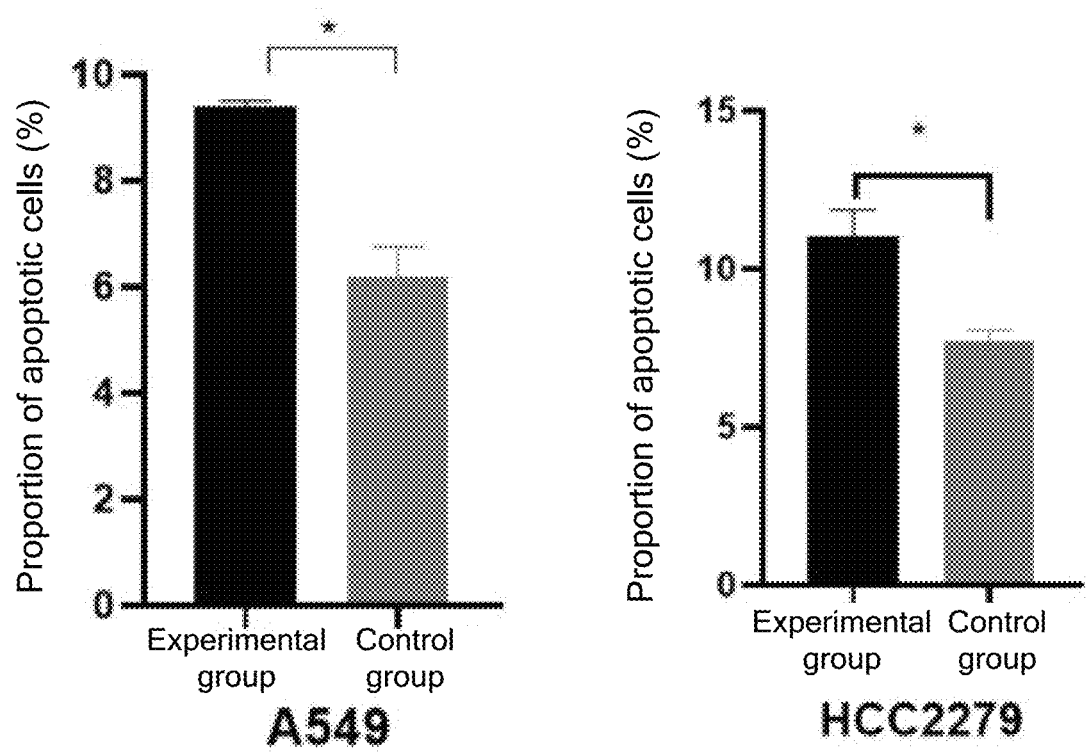
FIG. 9 is a schematic diagram of a statistical quantitative analysis results of an agonist on apoptosis of lung adenocarcinoma cells A549 and HCC2279 detected by a flow cytometry related in example 7 of the present disclosure.

As shown in FIGS. 8 and 9, an agonist constructed by the PIWI-interacting RNA piR-hsa-211106 can significantly cause the apoptosis of the lung adenocarcinoma cells.

Example 8

Figure 10:
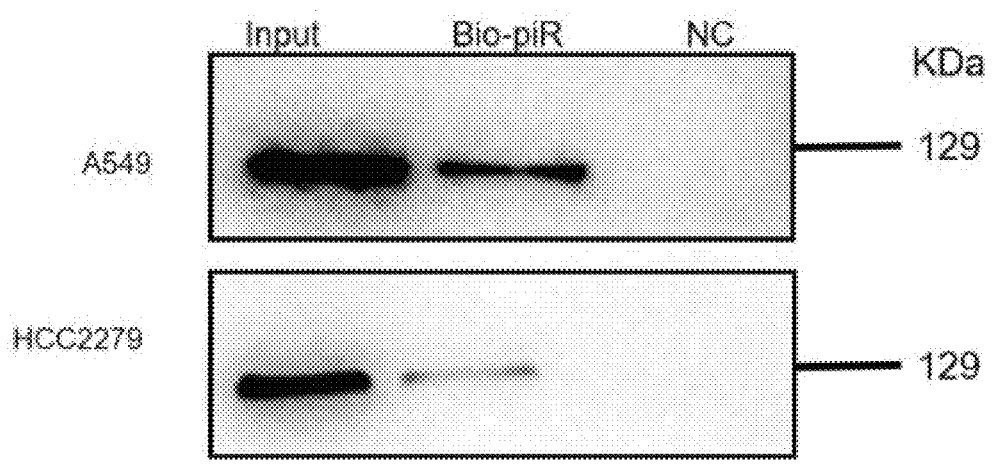
FIG. 10 is a schematic diagram of western blot (WB) results of a binding of a PIWI-interacting RNA piR-hsa-211106 with a pyruvate carboxylase related in example 8 of the present disclosure.

This example related to a process of a biotin-coupled probe RNA pull-down assay: $1 \times 10^7$ lung adenocarcinoma cells were harvested, lysed and subjected to an ultrasonic treatment, a biotinylated piR-hsa-211106 probe (Shanghai GenePharma Co., Ltd) and a probe-M280 streptavidin agarose bead (Invitrogen) were incubated at 25° C. for 2 h to generate a probe-coated magnetic bead, a mixture of a cell lysate and the probe-coated magnetic bead was incubated overnight at 4° C., after the mixture was washed with a washing buffer, a RNA complex bound to the bead was eluted, a purification was conducted with a Trizol reagent (Takara Biotechnology (Dalian) Co., Ltd) for a western blot (WB) analysis, and as shown in FIG. 10, the piR-hsa-211106 can bind to a pyruvate carboxylase.

Example 9

This example related to a RNA extraction and an analysis process of a gene expression level of lung adenocarcinoma cells:
  1 ml of Trizol was added to each well of a 6-well plate to lyse the cells and pipetted repeatedly with a pipette tip, after reaction at room temperature for 5 min, a lysate was transferred into a 1.5-ml centrifuge tube, 200 μl of chloroform was added, a tube cap was tightly covered, even mixing under a vortex was conducted, an mixture was allowed to stand at room temperature for 3 min, and centrifugation was conducted at 12,000 g/min and 4° C. for 15 min;
  an upper layer of aqueous phase liquid was transferred to a new 1.5-ml centrifuge tube, 500 μl of isopropanol was added, even mixing under a vortex was conducted, a mixture was allowed to stand at room temperature for 10 min, and centrifugation was conducted at 12,000 g/min and 4° C. for 10 min;
  a supernatant was pipetted and discarded, a white precipitate at a bottom part was preserved, 1 ml of 75% ethanol (prepared with DEPC water) was added, a white precipitate was gently flipped by hand, and centrifugation was conducted at 7,500 g/min and 4° C. for 5 min;
  the supernatant was discarded, a precipitate was dried at room temperature for 10-15 min and re-dissolved with 30-40 μl of DEPC water, and after a RNA concentration was detected, the RNA was stored in a −80° C. refrigerator or used directly; and
  1,000 ng of the extracted total RNA was subjected to reverse transcription into cDNA by using a reverse transcription kit (Takara Biotechnology (Dalian) Co., Ltd), according to an operation process of the kit, and the gene expression level was detected using a real-time fluorescent quantitative PCR technology by referring to an instruction of the kit.

Figure 11:
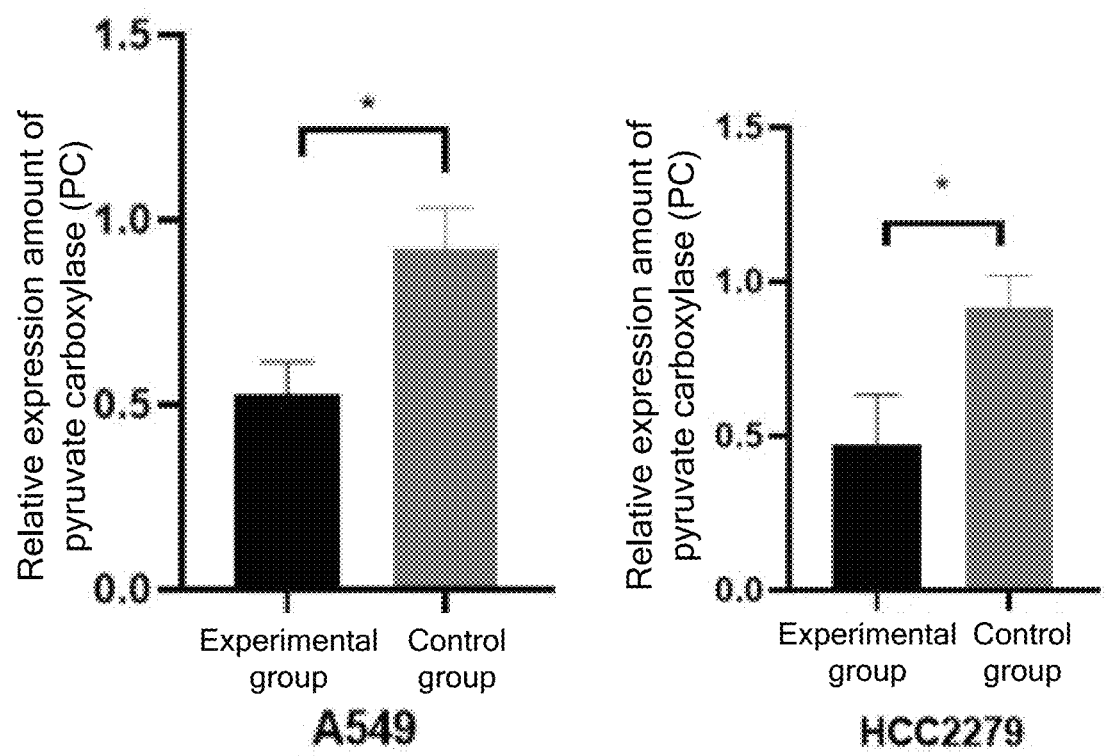
FIG. 11 is a schematic diagram of a qRT-PCR analysis of a PIWI-interacting RNA piR-hsa-211106 on a expression of pyruvate carboxylase related in example 9 of the present disclosure.

As shown in FIG. 11, a PIWI-interacting RNA piR-hsa-211106 can significantly inhibit an expression of a pyruvate carboxylase.

Example 10

This example related to an analysis process of a protein expression level of lung adenocarcinoma cells:
  Total proteins of the cells were extracted by using a radioimmunoprecipitation assay buffer (Dalian Meilunbio Co., Ltd) and a concentration of the proteins was adjusted to reach the same level by a BCA colorimetric method; and
  the protein samples were separated by an SDS-PAGE electrophoresis, the separated proteins were transferred to a PVDF membrane, the membrane was blocked with 5% powdered skim milk for 1 h, the membrane was washed, an incubation with a primary antibody (PC, GAPDH) was conducted overnight in a 4° C. refrigerator, the membrane was washed, an incubation with a secondary antibody was conducted at room temperature for 1 h, the membrane was washed, a target band was obtained by ECL chemiluminescence method, the band was subjected to a grayscale scanning by using a Quantity One software and a GAPDH internal reference was used for correction.

Figure 12:
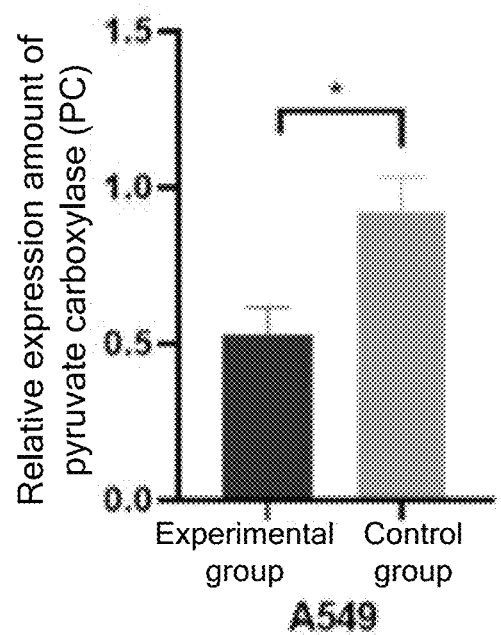
FIG. 12 is a schematic diagram of a WB analysis results of a PIWI-interacting RNA piR-hsa-211106 on a expression of pyruvate carboxylase related in example 10 of the present disclosure.
Figure 12:
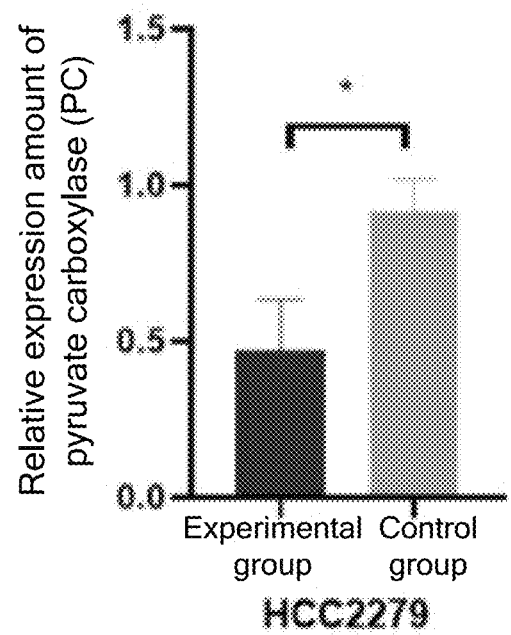

As shown in FIG. 12, a PIWI-interacting RNA piR-hsa-211106 can regulate an expression of a pyruvate carboxylase at a protein level, indicating that the PIWI-interacting RNA piR-hsa-211106 inhibits an energy metabolic pathway of the lung adenocarcinoma cells and promotes apoptosis of the lung adenocarcinoma cells.

Example 11

This example related to a process of constructing a tumor-bearing model of a nude mouse: 3- to 4-week-old BALB/c nude mice (SiPeiFu Laboratory Animal Technology Co., Ltd) were taken and used for an experiment after adapting to local conditions for 1 week, $2 \times 10^7$ of A549 cells were injected subcutaneously into left and right armpits of the mice, and when an implanted tumor reached 50 mm$^3$, a drug treatment was conducted.

Example 12

This example related to a drug-targeted treatment process of a tumor-bearing model of a nude mouse:

The nude mice were divided into two groups: a cisplatin experimental group and a normal saline control group, with 5 nude mice in each group;

The nude mice in the experimental group were injected intraperitoneally with cisplatin (5 mg/kg body weight/week), 50 μM of a PIWI-interacting RNA piR-hsa-211106 agonist was injected directly into a tumor on a right side and piR-NC (Shanghai GenePharma Co., Ltd) was injected into a tumor on a left side as a control group of the cisplatin treatment group;

An equal volume of normal saline was injected intraperitoneally into the nude mice in the control group, the PIWI-interacting RNA piR-hsa-211106 agonist was used to treat the tumor as above, the PIWI-interacting RNA piR-hsa-211106 agonist was used for treatment every other day for 28 days, and the tumor volume was measured once a week; the mice were sacrificed at an end of the experiment, and xenografts were peeled off and photographed.

Figure 13:
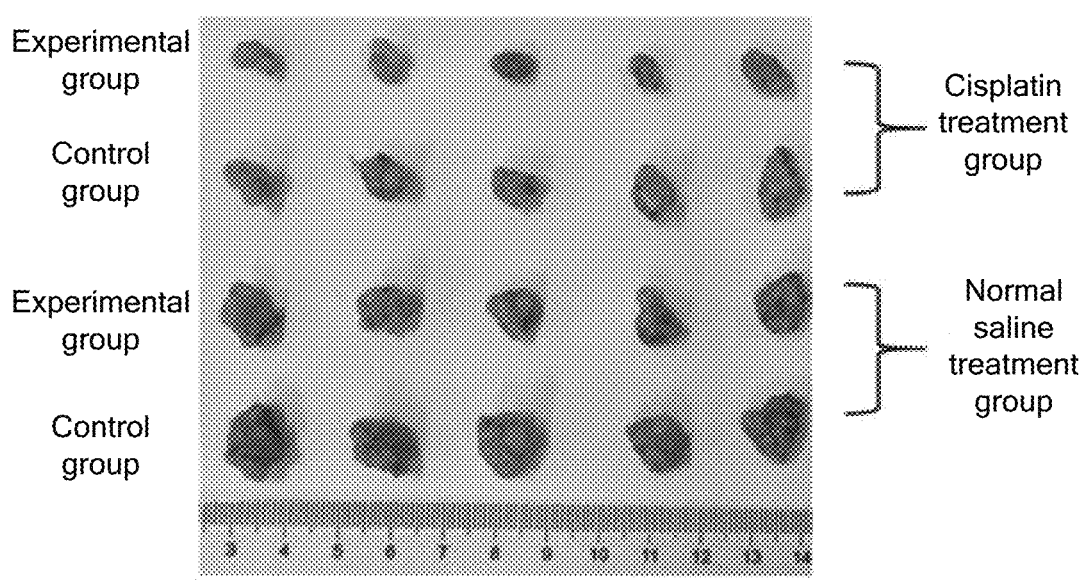
FIG. 13 is a schematic diagram of a tumor after a treatment of a PIWI-interacting RNA piR-hsa-211106 on tumor-bearing nude mice related in example 12 of the present disclosure.
Figure 14:
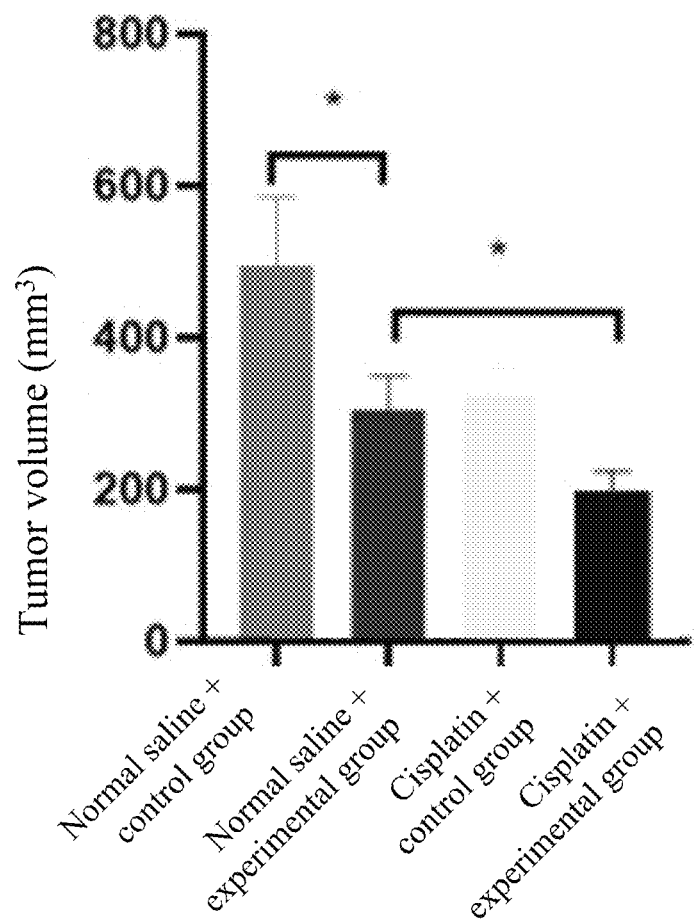
FIG. 14 is a statistical diagram of tumor volume after a treatment of a PIWI-interacting RNA piR-hsa-211106 on tumor-bearing nude mice related in example 12 of the present disclosure.
Figure 15:
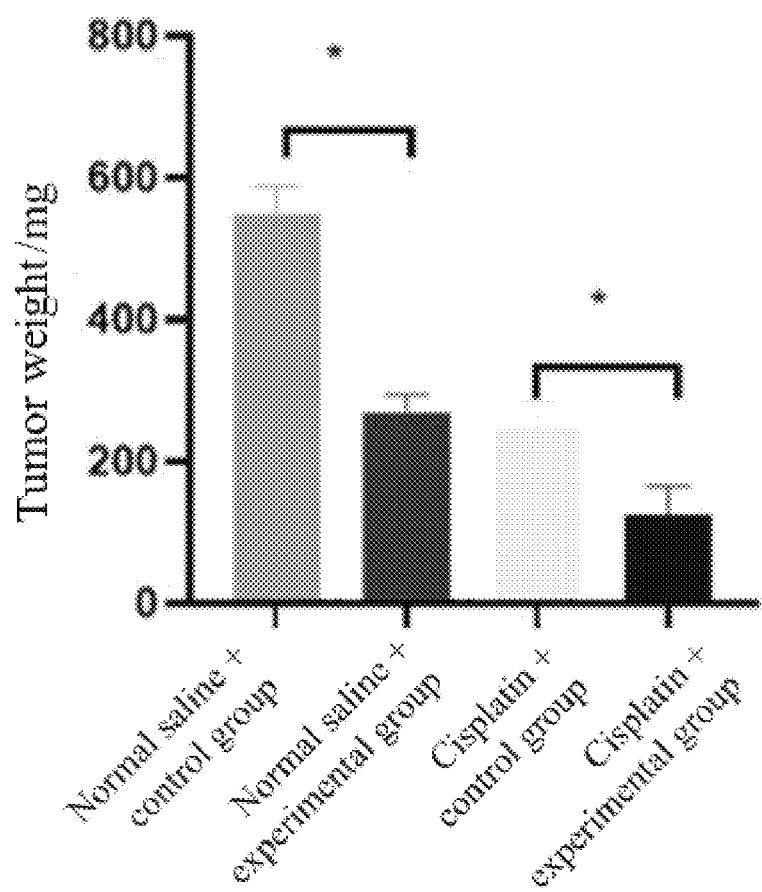
FIG. 15 is a statistical diagram of tumor weight after a treatment of a PIWI-interacting RNA piR-hsa-211106 on tumor-bearing nude mice related in example 12 of the present disclosure.

As shown in FIGS. 13, 14 and 15, the PIWI-interacting RNA piR-hsa-211106 has a comparable therapeutic effect as the positive control drug cisplatin (PDD), increases chemical sensitivity of the chemotherapeutic drug cisplatin and has a synergistic effect, indicating that the PIWI-interacting RNA piR-hsa-211106 is capable of inhibiting growth of lung adenocarcinoma in vivo.

Although a few embodiments of the present invention have been shown and described, it would be appreciated by those skilled in the art that changes may be made in this embodiment without departing from the principles and spirit of the invention, the scope of which is defined in the claims and their equivalents.

---

What is claimed is:

1. A method of inhibiting proliferation of lung adenocarcinoma cells A549 or HCC2279, comprising administering a therapeutic drug to the A549 or HCC2279 lung adenocarcinoma cells, wherein the therapeutic drug comprises PIWI-interacting RNA piR-hsa-211106 or a variant thereof that is greater than 80% identical to the entire length of SEQ ID NO:1.

2. The method according to claim 1, wherein the PIWI-interacting RNA piR-hsa-211106 or the variant thereof is encoded in a viral vector selected from the group consisting of an adenovirus, a lentivirus and an adeno-associated virus.

3. The method according to claim 2, wherein the nucleotide sequence of PIWI-interacting RNA piR-hsa-211106 is set forth in SEQ ID NO:1.

4. The method according to claim 1, wherein the method comprises transferring the PIWI-interacting RNA piR-hsa-211106 or the variant thereof into lung adenocarcinoma cells A549 or HCC2279 and determining an effect of the PIWI-interacting RNA piR-hsa-211106 or variant thereof on cell proliferation activity by detecting proliferation indicators of lung adenocarcinoma cells by a CCK8 kit and EdU staining.

5. The method according to claim 1, wherein the method comprises determining an effect of the PIWI-interacting RNA piR-hsa-211106 or the variant thereof on cell migration capacity by detecting migration indicators of lung adenocarcinoma cells.

* * * * *

SEQUENCE LISTING

```
<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: RNA sequence of PIWI-interacting RNA piR-hsa-
      211106

<400> SEQUENCE: 1
tccggctcga aggacttcgt ctgtaatttt                                         30

<210> SEQ ID NO 2
<211> LENGTH: 21
<212> TYPE: DNA
<213> ORGANISM: Artificial Sequence
<220> FEATURE:
<223> OTHER INFORMATION: Primer of piR-hsa-211106-F

<400> SEQUENCE: 2
ggctcgaagg acttcgtctg t                                                  21

<210> SEQ ID NO 3
<211> LENGTH: 20
<212> TYPE: DNA
<213> ORGANISM: Artificial Sequence
<220> FEATURE:
<223> OTHER INFORMATION: Primer of piR-hsa-211106-R

<400> SEQUENCE: 3
agtgcagggt ccgaggtatt                                                    20
```